United States Patent
Nijhawan

(10) Patent No.: US 10,561,694 B2
(45) Date of Patent: Feb. 18, 2020

(54) PHARMACEUTICAL COMPOSITIONS CONTAINING CANNABIS, USES THEREOF AND METHODS FOR IMPROVING SLEEP QUALITY

(71) Applicant: Exzell Pharma Inc., Markham (CA)

(72) Inventor: Pardeep Nijhawan, Markham (CA)

(73) Assignee: Exzell Pharma Inc., Markham (CA)

( * ) Notice: Subject to any disclaimer, the term of this patent is extended or adjusted under 35 U.S.C. 154(b) by 0 days.

(21) Appl. No.: 16/375,933

(22) Filed: Apr. 5, 2019

(65) Prior Publication Data

US 2019/0307825 A1  Oct. 10, 2019

(51) Int. Cl.
| | |
|---|---|
| *A61K 36/00* | (2006.01) |
| *A61K 36/185* | (2006.01) |
| *A61K 31/352* | (2006.01) |
| *A61K 31/192* | (2006.01) |
| *A61P 25/20* | (2006.01) |
| *A61K 31/05* | (2006.01) |
| *A61P 25/22* | (2006.01) |

(52) U.S. Cl.
CPC ............ *A61K 36/185* (2013.01); *A61K 31/05* (2013.01); *A61K 31/192* (2013.01); *A61K 31/352* (2013.01); *A61P 25/20* (2018.01); *A61P 25/22* (2018.01)

(58) Field of Classification Search
CPC ...................................................... A61K 36/00
USPC ........................................................ 424/725
See application file for complete search history.

(56) References Cited

U.S. PATENT DOCUMENTS

2003/0012824 A1 * 1/2003 Ott ........................ A61K 33/08
424/602

OTHER PUBLICATIONS

Cao, Xiao-Lan; Wang, Shi-Bin: Zhong, Bao-Liang; Zhang, Ling et al (Feb. 4, 2017). The prevalence of insomnia in the general population in China: A meta-analysis PLoS ONE 12(2)doi:10.1371/journal.pone.0170772.
NIH.gov Fact sheet Valerian; https://ods.od.nih.gov/factsheets/Valerian-HealthProfessional/ 9 pages.
NIH.gov Fact sheet Passiflora; U.S. Dept. of Health and Human Services; https://nccih.nih.gov/health/passionflower.
Michael J. Thorpy, Classification of Sleep Disorders, The American Society for Experimental Neuro Therapeutics, Inc. 20212, 9:687-701.

* cited by examiner

*Primary Examiner* — Michael V Meller
(74) *Attorney, Agent, or Firm* — Tysver Beck Evans

(57) ABSTRACT

A pharmaceutical composition containing cannabis for improving the quality of sleep in a patient is provided. Also provided are a use of the pharmaceutical composition for improving the quality of sleep in a patient, and methods for improving the quality of sleep. The pharmaceutical composition preferably includes a combination of therapeutically effective amounts of one or more of the following medicinal ingredients: cannabis, and/or an herb.

16 Claims, No Drawings

PHARMACEUTICAL COMPOSITIONS CONTAINING CANNABIS, USES THEREOF AND METHODS FOR IMPROVING SLEEP QUALITY

FIELD OF THE INVENTION

The present invention relates to pharmaceutical compositions containing cannabis and methods for improving the quality of sleep.

BACKGROUND OF THE INVENTION

There are an increasing number of patients who have trouble sleeping at night. This could be due to any of the following conditions: bruxism, night terrors, sleep apnea, narcolepsy, hypersomnia, cataplexy, restless leg syndrome, somniphobia, sleepwalking, shift work sleep disorder, and bed wetting. (See: American Academy of sleep Medicine (2001). The International Classification of Sleep Disorders, Revised (ICSD-R). ISBN 0-9657220-1-5) However, it has recently been noted that with the advent of new technologies such as smart devices and the increased stresses of living in a modern society, more and more normal individuals without the above conditions are also experiencing insomnia. A 2016 study from the Rand Corporation found the effects of sleep deprivation costs the United States (U.S.) up to $411 Billion a year. In addition, individuals who have sleep disorders have a shorter life expectancy.

Many individuals do not receive treatment for sleep disorders as they have not been properly diagnosed. The prevalence in the U.S. is estimated at 27.1% and 15% in China. (See: Cao, Xiao-Lan; Wang, Shi-Bin: Zhong, Bao-Liang; Zhang, Ling et al (2017 Feb. 4). "The prevalence of insomnia in the general population in China: A meta-analysis" PLoS ONE 12(2) doi:10.1371/journal.pone.0170772)

As common as the disorder is, the number of treatment options is limited. For example, patients who suffer from sleep apnea can use either a dental appliance or a continuous positive airway pressure (CPAP) machine to help. However, many patients find both apparatuses unpalatable and/or inconvenient. The dental appliance affects their jaws while the CPAP machine is large and noisy.

Other options for sleep disorders include the use of prescription drugs. These drugs include temazepam, triazolam, zaleplon, zolpidem, or trazodone are very effective in helping patients sleep but have many side effects. Side effects include the feeling of being sleepy all day, dependency, and cognitive impairment. The U.S. FDA warns that many patients should not use these drugs if they plan to drive the next day.

More natural options include melatonin. This is commonly used for patients who may want to prevent jet lag. The supplement has been shown to work well for short term use; however, no long-term data is available.

In addition to technology and stressors causing sleep impairment, drugs and alcohol also are known contributors. For example, cannabis is a drug that can cause or contribute sleep disorders. While cannabis helps induce sleep initially, it may often be challenging for patients to maintain sleep for the complete overnight period as drug levels drop and patients are unable to continue a restful night sleep.

What may be needed is a pharmaceutical composition of cannabis that promotes sleep and/or improves sleep quality while minimizing occurrences of low quality and/or restless periods of sleep.

SUMMARY OF THE INVENTION

According to an aspect of the present invention, there is disclosed a pharmaceutical composition for improving the quality of sleep and/or promoting a restful restorative sleep in a patient. The pharmaceutical composition may preferably, but need not necessarily, comprise alone or in combination, therapeutically effective amounts of cannabis and/or herbs for use as a medicinal product prescribed by a physician, a health care practitioner or an over-the-counter product available at pharmacies, marijuana dispensaries and/or mass food stores.

According to an aspect of the invention, there is preferably disclosed a pharmaceutical composition for improving the quality of sleep and/or promoting sleep in a patient. The pharmaceutical composition may preferably, but need not necessarily, additionally comprise therapeutically effective amounts of *Humulus lupulus*.

According to an aspect of the invention, there is preferably disclosed a pharmaceutical composition for improving the quality of sleep and/or calming the nerves and relaxing the body to promote sleep in a patient. The pharmaceutical composition may preferably, but need not necessarily, additionally comprise therapeutically effective amounts of *Melissa officinalis* (Lemon balm).

According to an aspect of the invention, there is preferably disclosed a pharmaceutical composition for improving the quality of sleep, having an anti-anxiety effect and/or promoting sleep in a patient. The pharmaceutical composition may preferably, but need not necessarily, additionally comprise therapeutically effective amounts of *Passiflora incarnata* (Passion Flower).

According to an aspect of the invention, there is preferably disclosed a pharmaceutical composition for improving the quality of sleep and/or promoting sleep in a patient. The pharmaceutical composition may preferably, but need not necessarily, additionally comprise therapeutically effective amounts of *Valeriana officinalis* (Valerian).

According to an aspect of the invention, there is preferably disclosed a pharmaceutical composition for improving the quality of sleep and/or promoting sleep in a patient. The pharmaceutical composition may preferably, but need not necessarily, comprise therapeutically effective amounts of Cannabis in any of the following form cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), a naphthoylindole, a phenylacetylindole, a benzoylindole, a cyclohexylphenole, delta-9 tetrahydrocannabinol (THC or dronabinol), delta-8 tetrahydrocannabinol (D8-THC), tetrahydrocannabinol acid (THCA), tetrahydrocannabivarin (THCV), tetrahydrocannabivarin acid (THCVA), the pharmaceutical agent is CBD, THC or a combination thereof.

According to an aspect of the invention, there is preferably disclosed a pharmaceutical composition for improving the quality of sleep in a patient. The pharmaceutical composition may preferably, but need not necessarily, comprise a pharmaceutically acceptable excipient selected from any of the group consisting of: hydroxypropylcellulose, starch, silicon dioxide, gelatin, magnesium stearate, and/or microcrystalline cellulose.

According to an aspect of the invention, there is preferably disclosed a pharmaceutical composition for improving the quality of sleep in a patient. The pharmaceutical composition may preferably, but need not necessarily, comprise the form of a tablet, caplet, capsule, dermal patch, oil drops, powder or a suspension.

Other advantages, features and characteristics of the present invention, as well as methods of use and applications of the related elements of the pharmaceutical composition and formulation will become more apparent upon consideration of the following detailed description and the appended claims, the latter of which are briefly described hereinbelow.

DETAILED DESCRIPTION OF THE PREFERRED EMBODIMENTS

The description that follows, and the embodiments described therein, is provided by way of illustration of an example, or examples, of particular embodiments of the principles and aspects of the present invention. These examples are provided for the purposes of explanation, and not of limitation, of those principles and of the invention.

It should also be appreciated that the present invention can be implemented in numerous ways, including as a use of the pharmaceutical composition or a method for improving the quality of sleep. In this specification, these implementations, or any other form that the invention may take, may be referred to as uses or methods. In general, the order of the steps of the disclosed methods may be altered within the scope of the invention.

In this disclosure, a number of terms are used. The following definitions of such terms are provided.

As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

As used herein, the skilled reader may generally understand the term "sleep" to generally mean a naturally recurring state of mind and body, characterized by altered consciousness, relatively inhibited sensory activity, inhibition of nearly all voluntary muscles, and reduced interactions with surroundings. Persons skilled in the relevant art will appreciate that sleep occurs in repeating periods, in which the body alternates between two distinct modes: rapid eye movement ("REM") sleep and non-REM sleep. During sleep, most of the body's systems are in an anabolic state, helping to restore the immune, nervous, skeletal, and muscular systems; which are vital processes that maintain mood, memory, and cognitive function and play a large role in the function of the endocrine and immune systems. Skilled readers will understand that the "quality of sleep" or "sleep quality" may be evaluated from an objective and a subjective point of view. Objective sleep quality refers to how difficult it is for a person to fall asleep and remain in a sleeping state, and how many times they wake up during a single night. Poor sleep quality disrupts the cycle of transition between the different stages of sleep. Subject sleep quality refers to a sense of being rested and regenerated after awaking from sleep. Persons skilled in the relevant art may associate considerations such as restful restorative sleep, sleep that provides an individual with sleep benefits (e.g., maintenance of mood, memory, cognition, etc.), calming the nerves and relaxing the body prior to sleep, and/or anti-anxiety state prior to sleep.

As used herein, a person skilled in the relevant art may generally understand the term "treatment" to generally refer to an approach for obtaining beneficial or desired results. Beneficial or desired results can include, but are not limited to, prevention or prophylaxis, alleviation or amelioration of one or more symptoms or conditions, diminishment of the extent of a disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a person skilled in the relevant art may generally understand the term "therapeutically effective amount" to be an amount sufficient to effect treatment when administered to a subject in need of treatment. In the case of the embodiments of the present invention, a therapeutically effective amount can include, but is not limited to, an amount that improves the quality of sleep from an objective and/or subjective point-of-view.

It will be understood by a person skilled in the relevant art that the compositions of the present invention can be formulated into pharmaceutical compositions for administration in a manner customary for administration of such materials using standard pharmaceutical formulation, chemistries and methodologies, all of which are readily available to a person skilled in the relevant art. It will also be understood by a person skilled in the relevant art that such pharmaceutical compositions may include one or more excipients, carriers, stabilizers or other pharmaceutically inactive compounds, such as, but not limited to, wetting or emulsifying agents, pH buffering substances, hydroxypropylcellulose, starch, silicon dioxide, gelatin, magnesium stearate, microcrystalline cellulose and the like. Pharmaceutically acceptable salts can also be included therein. A thorough discussion of pharmaceutically acceptable excipients, vehicles and auxiliary substances is available in Remington's. Pharmaceutical Sciences (Mack Pub. Co. N.J. 1991). Such pharmaceutical compositions can be prepared as oral or transdermal preparations. The therapeutically effective doses may vary according to body weight and the timing and duration of administration will be determined by specific clinical research protocols.

It will be understood by a person skilled in the relevant art that the term "dose" refers to the measured quantity of an agent, preferably a therapeutic agent, to be taken at one time to have a desired therapeutic effect(s). Preferably, "dose" as used herein means a specified quantity of a pharmaceutical or therapeutic agent provided in one or more administration. It will be further understood that a "dosage unit" or "dosage form" as used herein means a form in which the active agent is provided. It will be understood that any known dosage form may be employed with the present invention. These may include, solid dosage forms, liquid dosage forms, gel dosage forms, etc. The term "effective dose" or "effective dosage" is defined as an amount sufficient to achieve or at least partially achieve the desired effect. The term "therapeutically effective dose" is defined as an amount sufficient to cure or at least partially arrest the disease and/or one of more associated symptoms in a patient already suffering from the disease.

It will be understood by a person skilled in the relevant art that the term "administering" means providing a therapeutically active agent or composition to a subject, and includes, but is not limited to, administering by a medical professional and self-administering.

It will be understood by a person skilled in the relevant art that a "pharmaceutical agent" or "therapeutic agent" as used herein means a substance that provides a therapeutic effect when administered to a subject. "Pharmaceutical composition" means a mixture of substances suitable for administering to an individual that includes one or more pharmaceutical or therapeutically effective agents. The terms "active pharmaceutical ingredient" shall be understood to refer to a substance in a pharmaceutical composition that provides a desired effect.

The improvement of sleep quality in accordance with the present invention and as hereinafter defined for the purposes of this invention is directed to sleep induction and maintenance of sleep during an overnight period including the improvement in subjective and/or objective measures of sleep quality. Stress and/or anxiety, including the symptoms associated therewith, may be caused or mediated at least in part by stress, anxiety and/or nervous tension. In a preferred embodiment of the present invention, an agent or agents which can improve the quality of sleep including objective and/or subjective measures thereof is recommended. Since no single active ingredient is presently capable of improving the quality of sleep, a pharmaceutical composition such as is described in the present invention is recommended.

Preferred embodiments of the present invention improve the quality of sleep in a patient including one or more subjective and/or objective measures of sleep quality.

Preferably, the pharmaceutical compositions of the present invention may be provided with different active ingredients, different strengths and/or different formulations. Preferably, the pharmaceutical composition of the present invention comprises a therapeutically effective amount of cannabis. A person skilled in the relevant art would understand the term "cannabis" to refer to a genus of flowering plants in the family Cannabaceae which produce a group of chemicals called cannabinoids that produce physiological effects when administered to a patient. Persons skilled in the art will also readily appreciate that a cannabinoid is one of a class of diverse chemical compounds that acts on cannabinoid receptors (e.g., cannabinoid receptor type 1, cannabinoid receptor type 2) in cells that alter neurotransmitter release in the brain. In accordance with one or more preferred embodiments of the invention, the pharmaceutical composition may comprise cannabis-derived cannabinoids selected from the group consisting of: cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), a naphthoylindole, a phenylacetylindole, a benzoylindole, a cyclohexylphenole, delta-9 tetrahydrocannabinol (THC or dronabinol), delta-8 tetrahydrocannabinol (D8-THC), tetrahydrocannabinol acid (THCA), tetrahydrocannabivarin (THCV), tetrahydrocannabivarin acid (THCVA), the pharmaceutical agent is CBD, THC or combinations thereof. In accordance with an aspect of the present invention, compositions comprising a therapeutically effective amount of cannabis may preferably serve to improve the quality of sleep in a patient. In accordance with some embodiments of the present invention, cannabis may be present in the composition in a particulate form with at least 50% by wt of the particles ranging in size from about 50 micron to about 2000 micron and wherein the particles comprise a cannabinoid, cannabinoid derivative, a terpene or a mixture thereof in a range of about 1 mg to about 30 mg of cannabinoid (CBD or THC) and most preferably from about 2 mg to about 20 mg per dose.

The pharmaceutical composition of the present invention may also comprise a therapeutically effective amount of one or more herbs, including but not limited to: Lemon balm (*Melissa officinalis*); Passion flower (*Passiflora incarnata*); Valerian; Hops (*Humulus lupulus*); and combinations thereof.

In a preferred embodiment, the pharmaceutical composition of the present invention comprises a therapeutically effective amount of Lemon balm (*Melissa officinalis*). Persons skilled in the relevant art would understand the term "Lemon balm" to be a perennial herbaceous plant in the mint family Lamiaceae. Lemon balm leaves may have been used in the prior art as traditional medicine—as a tea, externally applied, or as an essential oil—in the treatment of disorders of the gastrointestinal tract, nervous system, liver, and bile. It has been reported that Lemon balm may also have been used in the prior art for cognitive purposes (e.g., the improvement of cognition and reduction in stress and anxiety) and to calm the nerves and to relax the body and hence help for stress and anxiety (See: NIH.gov Fact sheet *Melissa officinalis*). In accordance with an aspect of the present invention, compositions comprising a therapeutically effective amount of Lemon balm may preferably serve to improve the quality of sleep. In accordance with some embodiments of the present invention, Lemon balm may be present in the composition from about 25 mg to about 1600 mg per dose and most preferably from about 50 mg to about 100 mg per dose.

In a preferred embodiment, the pharmaceutical composition of the present invention comprises a therapeutically effective amount of Passion flower (*Passiflora incarnata*). Persons skilled in the relevant art would understand the term "Passion flower" to be a perennial and member of the passionflower genus *Passiflora*. Passion flower may have been used in the prior art as a traditional remedy for anxiety, insomnia, hypertension, or as an antitussive. It has been reported that passion flower may exhibit sedative and anti-anxiety activity in tests involving laboratory animals. Human studies of *Passiflora*, in certain combination products, may have also demonstrated anti-anxiety and sedative properties. In addition, it has been reported that passion flower may have effects that are similar to benzodiazepines (e.g., diazepam [Valium™]) and monoamine oxidase inhibitors or MAOIs (e.g., selegiline). Passion flower has been reported to provide a calming, sleep inducing, and muscle spasm relieving effects. (See: NIH.gov Fact sheet *Passiflora*) In accordance with an aspect of the present invention, compositions comprising a therapeutically effective amount of Passion flower may preferably serve to enhance the quality of sleep. In accordance with some embodiments of the present invention, Passion flower may be present in the composition from about 25 mg to about 3000 mg per dose and most preferably from about 30 mg to about 70 mg per dose.

In a preferred embodiment, the pharmaceutical composition of the present invention comprises a therapeutically effective amount of Valerian (*Valeriana officinalis*, setwall, Valerianae radix, Baldrianwurzel, and phu). Persons skilled in the relevant art would understand the term "Valerian" to be a member of the Valerianaceae family perennial flowering plant native to Europe and Asia (and naturalized in North America) with heads of sweetly scented pink or white flowers that bloom in the summer. Persons skilled in the art will also appreciate that Valerian has a distinctive odour that may be unpleasant. It has been reported that Valerian may have been used as in the prior art as a herbal medicine for treating insomnia, restless leg syndrome, anxiety, and to relieve mild symptoms of mental stress and to aid sleep. Although the genus Valerian includes over 250 species, *V. officinalis* is the species most often used in the United States and Europe. (See: NIH.gov Fact sheet Valerian) In accordance with an aspect of the present invention, compositions comprising a therapeutically effective amount of Valerian may preferably serve to enhance the quality of sleep. In accordance with some embodiments of the present invention, Valerian may be present in the composition from about 100 mg to about 3000 mg per dose and most preferably from about 125 mg to about 175 mg per dose.

In a preferred embodiment, the pharmaceutical composition of the present invention comprises a therapeutically effective amount of hops (*Humulus lupulus*). Persons skilled in the relevant art would understand the term "hops" to be a species of flowering plant in the Cannabaceae family, native to Europe, western Asia and North America. Hops are a dioecious, perennial, herbaceous climbing plant which sends up new shoots in early spring and dies back to a cold-hardy rhizome in autumn. Skilled readers will appreciate that hops are described as bine plants rather than vine because, unlike vines, they have stiff downward facing hairs that provide stability and allow them to climb. These shoots allow *H. lupulus* to grow anywhere from 4.6 to 6.1 metres (15 to 20 ft). Hops have fragrant, wind-pollinated flowers that attract butterflies. It has been reported that hops have been shown to be beneficial in helping as a sleep aid. (See: NIH.gov Fact sheet *Humulus*) In accordance with an aspect of the present invention, compositions comprising a therapeutically effective amount of hops may preferably serve to enhance the quality of sleep. In accordance with some embodiments of the present invention, hops may be present in the composition from about 2 mg to about 400 mg per dose and most preferably from about 50 mg to 100 mg per dose.

Persons skilled in the relevant art may appreciate that cannabis helps to induce sleep initially; however, it has been reported that patients using cannabis to induce sleep find it challenging to have a complete night sleep as drug levels drop and patients are unable to continue a restful sleep overnight.

In preferred embodiments of the present invention, the combination of cannabis and/or herbs provides advantageous outcomes as the pharmaceutical composition may retain the therapeutic benefits of cannabis on inducing sleep while maintaining a restful overnight sleep and minimizing its potential adverse effects. Patients administered the pharmaceutical composition of the present invention tend to experience a full restorative night of sleep.

The pharmaceutical composition may preferably, but need not necessarily, be administered in a single dose prior to bed time. In a preferred embodiment, a dose is taken once daily prior to bed. In preferable embodiments, a dosing regimen is continued until sleep quality has improved. In some embodiments, the composition of the present invention may be administered once daily to reduce the likelihood of experiencing low quality sleep.

In a preferred embodiment, the pharmaceutical composition of the present invention is used as a nutritional supplement to help patients who suffer from mild to moderate sleep disorders improve the quality of sleep they experience. The pharmaceutical composition of the present invention will preferably, but need not necessarily, increase the amount, frequency and/or duration of REM sleep. Preferably, the disorders that may be treated by embodiments of the present invention include, but are not limited to, bruxism, night terrors, sleep apnea, narcolepsy, hypersomnia, cataplexy, restless leg syndrome, somniphobia, sleepwalking, shift work sleep disorder, and bed wetting. The pharmaceutical composition of the present invention is preferably formulated in multiple strengths to treat the symptoms associated with the above disorders and/or decrease the number of times a patient awakens overnight. The pharmaceutical composition of the present invention is preferably formulated to use the minimal therapeutically effective doses of the active ingredients to maximize absorption in the gastrointestinal track (e.g., maximize bioavailability) and minimize side effects. In accordance with a preferred embodiment of the present invention, the pharmaceutical composition allows for a reduction in the dose of cannabis required to achieve the same therapeutic effect compared to cannabis administered to a patient in a traditional dosage form (e.g., smoking or inhalation).

In accordance with a preferred embodiment of the present invention, the pharmaceutical composition is formulated to contain cannabis comprising a higher dose of CBD (cannabidiol) or from about 2 mg to about 20 mg per dose. An advantage of such formulations is to promote the onset of sleep and contribute to the maintenance of sleep throughout an overnight period.

In accordance with a preferred embodiment of the present invention, the administration of lower doses of cannabis (compared to cannabis administered in a traditional dosage form, for example, smoking or inhalation) combined with the herbs disclosed herein is advantageous as it provides a therapeutic effect on improving the quality of sleep and a reduction in cravings for further cannabis that chronic cannabis users may experience.

In accordance with a preferred embodiment of the present invention, the combination of cannabis and/or herbs disclosed herein is advantageous as it may provide an unexpected synergistic therapeutic effect on improving the quality of sleep.

In accordance with a preferred embodiment of the present invention, the combination of cannabis and/or herbs disclosed herein is advantageous as it may unexpectedly allow for the use of a lower dose of cannabis to achieve a similar therapeutic effect when compared to cannabis administered to a patient in a traditional dosage form (e.g., smoking or inhalation).

In accordance with a preferred embodiment of the present invention, the combination of cannabis and/or herbs disclosed herein is advantageous as it may allow for the use of a lower dose of cannabis to reduce the severity and/or number of potential cannabis-related adverse effects.

The pharmaceutical composition of the present invention is a formulation comprising cannabis in addition to various herbs, either used as a medicine prescribed by a physician, a health care practitioner, or an over-the-counter product available in pharmacies, marijuana dispensaries, and mass food stores and will preferably help patients who suffer from sleeping disorders achieve more restful and complete sleep.

In accordance with a preferred embodiment of the present invention, the pharmaceutical composition comprising cannabis and/or herbs may be administered prior to bed time to improve sleep quality during an overnight period. The pharmaceutical composition of the present invention delivers high concentrations of several herbs including *Passiflora incarnata* (passion flower), *Melissa officinalis* (lemon balm), *Valeriana officinalis*, *Humulus lupulus* and therapeutically effective concentrations of cannabis in any form without causing increased side effects. The combination of the foregoing herbs and cannabis in a single formulation for improving the quality of sleep in a patient is unique and has not been previously described.

EXAMPLE 1

The following example sets out a preferred formulation of the pharmaceutical composition in accordance with the present invention for improving the quality of sleep in a patient.

| Medicinal Ingredients | Quantity | Extract |
|---|---|---|
| *Humulus lupulus* | 85.0 mg | 4:1 DHE: 340 mg |
| *Melissa officinalis* | 75.0 mg | 8:1 DHE: 600 mg |
| *Passiflora incarnata* | 50.0 mg | 6:1 DHE: 300 mg |
| *Valeriana officinalis* | 150.0 mg | 4:1 DHE: 600 mg |
| *Cannabis* | 25 mg | Pharmaceutical-grade *cannabis* with a THC (delta-9-tetrahydrocannabinol content of 9.4% |

In preferred embodiments of the invention, the formulation is allergen free (e.g., egg products, wheat (gluten) and dairy (lactose)). In addition, all compounds in the formulation are preferably gluten free.

EXAMPLE 2

Background:
A test formulation comprising a combination of *Humulus lupulus* (85.0 mg), *Melissa officinalis* (75.0 mg), *Passiflora incarnata* (50.0 mg), *Valeriana officinalis* (150.0 mg), and *Cannabis* (25 mg) was prepared in a capsule dosage form to study the effectiveness of the combination on improving the quality of sleep.

Objective:
To assess whether the test formulation described above is effective in improving the quality of sleep.

Methods:
A 40 year old female is not able to sleep at night. The subject was administered the test formulation once daily before bedtime for 10 days and then qualitatively assessed for sleep quality.

Results:
The subject experienced an ability to initiate and maintain sleep for a full night. No obvious adverse effects of the test formulation were identified.

CONCLUSIONS

The test formulation may be effective in improving the quality of sleep. Further studies may be needed to qualitatively and/or quantitatively assess improvement in sleep quality and to determine the preferred medicinal ingredients (including the preferred quantity of each) to include in the composition as well as the potential adverse effects associated with same.

The above description is meant to be exemplary only, and one skilled in the art will recognize that changes may be made to the embodiments described without departing from the scope of the invention disclosed. Modifications which fall within the scope of the scope of the present invention will be apparent to those skilled in the art, in light of a review of this disclosure, and such modifications are intended to fall within the appended claims.

This concludes the description of presently preferred embodiments of the invention. The foregoing description has been presented for the purpose of illustration and is not intended to be exhaustive or to limit the invention to the precise form disclosed. Other modification, variations and alterations are possible in light of the above teaching and will be apparent to those skilled in the art, and may be used in the design and manufacture of other embodiments according to the present invention without departing from the spirit and scope of the invention. It is intended the scope of the invention be limited not by this description but only by the claims forming a part hereof

What is claimed is:

1. A tablet, caplet, capsule or dermal patch consisting essentially of a cannabis extract, a lemon balm extract, a passion flower extract, and a valerian extract.

2. The tablet, caplet, capsule or dermal patch of claim 1, wherein the tablet, caplet, capsule or dermal patch consists essentially of from about 25 mg to about 1600 mg of the lemon balm extract per dose; from about 25 mg to about 3000 mg of the passion flower extract per dose; and from about 100 mg to about 3000 mg of the valerian extract per dose.

3. The tablet, caplet, capsule or dermal patch of claim 1, wherein the tablet, caplet, capsule or dermal patch consists essentially of from about 50 mg to about 1000 mg of the lemon balm extract per dose; from about 30 mg to about 70 mg of the passion flower extract per dose; and from about 125 mg to about 175 mg of the valerian extract per dose.

4. The tablet, caplet, capsule or dermal patch of claim 1, wherein the tablet, caplet, capsule or dermal patch consists essentially of from about 25 mg to about 1600 mg of the lemon balm extract per dose.

5. The tablet, caplet, capsule or dermal patch of claim 1, wherein the tablet, caplet, capsule or dermal patch consists essentially of from about 25 mg to about 3000 mg of the passion flower extract per dose.

6. The tablet, caplet, capsule or dermal patch of claim 1, wherein the tablet, caplet, capsule or dermal patch consists essentially of from about 100 mg to about 3000 mg of the valerian extract per dose.

7. The tablet, caplet, capsule or dermal patch of claim 1, wherein the tablet, caplet, capsule or dermal patch consists essentially of from about 1 mg to about 30 mg of the cannabinoid extract per dose.

8. The tablet, caplet, capsule or dermal patch of claim 1, wherein the tablet, caplet, capsule or dermal patch consists essentially of from about 2 mg to about 20 mg of the cannabinoid extract per dose.

9. A tablet, caplet, capsule or dermal patch consisting essentially of a cannabis extract, a lemon balm extract, a passion flower extract, a valerian extract and a hops extract.

10. The tablet, caplet, capsule or dermal patch of claim 9 wherein the tablet, caplet, capsule or dermal patch consists essentially of from about 25 mg to about 1600 mg of the lemon balm extract per dose; from about 25 mg to about 3000 mg of the passion flower extract per dose; from about 100 mg to about 3000 mg of the valerian extract per dose and from about 2 mg to 400 mg of the hops extract per dose.

11. The tablet, caplet, capsule or dermal patch of claim 9 wherein the tablet, caplet, capsule or dermal patch consists essentially of from about 50 mg to about 1000 mg of the lemon balm extract per dose; from about 30 mg to about 70 mg of the passion flower extract per dose; from about 125 mg to about 175 mg of the valerian extract per dose; and from about 50 mg to about 100 mg of the hops extract per dose.

12. The tablet, caplet, capsule or dermal patch of claim 9 wherein the tablet, caplet, capsule or dermal patch consists essentially of from about 25 mg to about 1600 mg of the lemon balm extract per dose.

13. The tablet, caplet, capsule or dermal patch of claim 9 wherein the tablet, caplet, capsule or dermal patch consists essentially of from about 25 mg to about 3000 mg of the passion flower extract per dose.

14. The tablet, caplet, capsule or dermal patch of claim 9 wherein the tablet, caplet, capsule or dermal patch consists essentially of from about 100 mg to about 3000 mg of the valerian extract per dose.

15. The tablet, caplet, capsule or dermal patch of claim 9 wherein the tablet, caplet, capsule or dermal patch consists essentially of from about 1 mg to about 30 mg of the cannabinoid extract per dose.

16. The tablet, caplet, capsule or dermal patch of claim 9 wherein the tablet, caplet, capsule or dermal patch consists essentially of from about 2 mg to 400 mg of the hops extract per dose.

\* \* \* \* \*